United States Patent

Nadolsky et al.

Patent Number: 4,719,282
Date of Patent: Jan. 12, 1988

[54] POLYCATIONIC BLOCK COPOLYMER

[75] Inventors: Richard J. Nadolsky, Clarksburg; Bharat B. Desai, Belle Mead, both of N.J.

[73] Assignee: Miranol Inc., Dayton, N.J.

[21] Appl. No.: 855,118

[22] Filed: Apr. 22, 1986

[51] Int. Cl.$^4$ .................. C08G 69/00; C08G 69/02
[52] U.S. Cl. ........................... 528/310; 210/702; 252/89.1; 428/411; 528/271; 528/367; 528/369
[58] Field of Search .............. 528/310, 271, 367, 369; 252/89.1; 210/702; 428/411

[56] References Cited

U.S. PATENT DOCUMENTS

| | | | |
|---|---|---|---|
| 4,166,894 | 9/1979 | Schaper | 528/310 |
| 4,254,255 | 3/1981 | Löbach et al. | 528/310 |
| 4,348,514 | 9/1982 | Löbach et al. | 528/310 |
| 4,384,110 | 5/1983 | Löbach et al. | 528/310 |

*Primary Examiner*—Harold D. Anderson
*Attorney, Agent, or Firm*—Ladas & Parry

[57] ABSTRACT

Novel polycationic block copolymers useful as antistatic agents in detergent formulations and as flocculating agents are obtained by first forming a block of units by reacting a monomer of the formula II

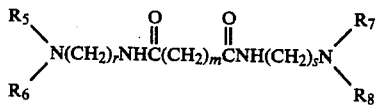

wherein
each of $R_5$, $R_6$, $R_7$ and $R_8$ may be the same or different and is selected from the group consisting of $C_{1-3}$ alkyl, $C_{1-3}$ hydroxy alkyl and polyoxyalkylene,
m is an integer from 0 to 34 and
r and s are the same or different and are integers from 1 to 6,
with a molar excess of a dihalide of the formula

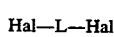

wherein Hal represents a halogen atom and L is selected from

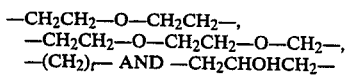

where t is an integer from 2 to 6 and thereafter reacting the product so formed with a compound of the formula III

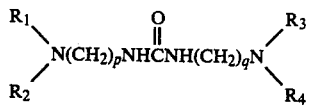

wherein $R_1$, $R_2$, $R_3$ and $R_4$ are each individually selected from the group consisting of $C_{1-3}$ alkyl, $C_{1-3}$ hydroxyalkyl and polyoxyalkylne and p, and q are each individually integers of form 1 to 6 and, if necessary, in order to ensure a total molar ratio of compounds of Formula II and III to those of the formula Hal—L—Hal of 1:1 reacting the product with further compound of the formula Hal—L—Hal.

16 Claims, No Drawings

POLYCATIONIC BLOCK COPOLYMER

BACKGROUND OF THE INVENTION

1. Field of the Invention

The present invention relates to novel polycationic block copolymers of use inter alia as antistatic aids in detergent formulations and as flocculating agents.

2. Prior Art

Polymeric quaternary ammonium compounds have been known for many years. For example U.S. Pat. No. 2,261,002 describes such compounds as having use as photographic chemicals, pesticides, pour point depressants, pigment dispersion control agents and surface active agents.

U.S. Pat. No. 3,632,559 (Matter, issued Jan. 4, 1972) describes cationically active water soluble polyamides obtained by alkylation of a polyamide with a bifunctional alkylation agent.

U.S. Pat. No. 4,166,894 (Schaper Sept. 4, 1979) describes functional ionene polymer compositions of use as wet and dry strength additives, corrosion inhibitors and electroconductive coatings.

U.S. Pat. No. 3,734,889 of Lipowski et al describes the production of quaternary aminoplast polymers by reaction of for example dimethylamino propylamine with adipic acid followed by chain extension with for example dichloroethyl ether. Most of the products obtained are of relatively low molecular weight although reference is made to products containing up to 1,000 repeating units. The products are not block copolymers and are useful as flocculants, drainage aids and as dry strength resins in paper manufacture. U.S. Pat. No. 4,505,833 of Mar. 19, 1985 also to Lipowski et al describes the use of such products to prevent, inhibit or reduce swelling or migrating of clay particles in a clayey geological formation.

British Patent Application No. 2,066,663 A in the name of L'Oreal (apparently equivalent to U.S. Pat. No. 4,517,174 of May 14, 1985) describes a wide variety of quaternary polymers of use in cosmetics. Included among the products of that invention are in Example 45 condensation copolymers containing alternating units derived from a ditertary amine and a dihalide of the formula:

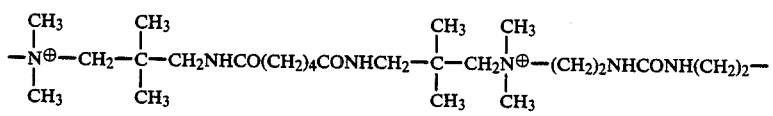

So far as applicants are aware, however, there has been no previous suggestion of the utility of polycationic block copolymers wherein the blocks are of different types of monomer units.

U.S. Pat. No. 4,157,388 of Christiansen describes compositions containing polyquaternary ammonium compounds for use as hair conditioners and antistats and humectants for fibrous textile products. The products are polymers formed by quaternizing the product of a reaction between tertiary amines and urea with a dihalide. If desired one can link blocks of units of the products obtained using one particular amine to blocks wherein a different amine is employed. These compounds are generally liquid at room temperature. Mirapol® A-15 is a compound in accordance with Examples of Christiansen having the formula:

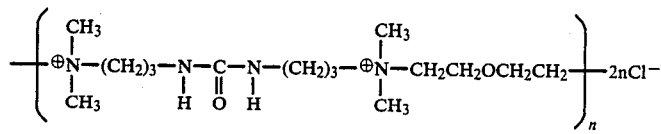

wherein n is at least one.

In commonly assigned copending application Ser. No. 758483 filed on July 24, 1985 which is a continuation in part of application Ser. No. 485197 filed on Apr. 15, 1983, now abandoned, there are described products of the general Formula:

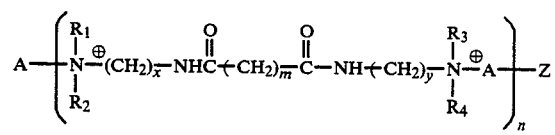

wherein $R_1$, $R_2$, $R_3$ and $R_4$ may be the same or different and are selected from the group consisting of hydrogen, methyl, ethyl, propyl, $-CH_2CH_2OH$, $-CH_2CH(OH)CH_3$ and $-CH_2CH_2(OCH_2CH_2)_pOH$ wherein p is an integer from 0 to 6 with the proviso that not all of $R_1$, $R_2$, $R_3$ and $R_4$ are hydrogen;

x and y are the same or different and are an integer from 1 to 6;

n is a value such that the number average molecular weight of the product is in excess of 20,000;

m is an integer from 0 to 34, for example 3-10, typically 4-7;

X is halogen;

Z is halogen or amino-diamido ammonium residue; and

A is the residue of a dihalide.

BRIEF DESCRIPTION OF THE PRESENT INVENTION

It is an object of the present invention to produce polycationic block copolymers having useful properties.

It is another object of the present invention to provide a polycationic product that is compatible with anionic detergent formulations.

It is a further object of the present invention to provide a product having good antistatic properties.

It is a yet further object of the present invention to provide a product that has such properties and is also a good flocculating agent.

According to the present invention we provide block copolymers of the configuration:

$$[Q_wL(AL)_x(BL)_yQ_w]^{2(x+y)}+2(x+y)D^-$$ Formula I wherein
A is

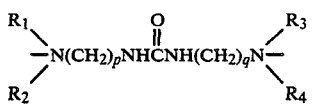

and B is

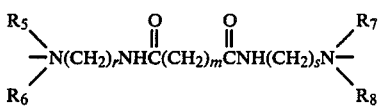

wherein:
$R_1$, $R_2$, $R_3$, $R_4$, $R_5$, $R_6$, $R_7$, $R_8$ may be the same or different and are generally selected from the group consisting of $C_1$-$C_3$ alkyl, $C_1$-$C_3$ hydroxyalkyl, or hydroxy polyalkylene;

p, q, r and s are the same or different and are an integer from 1 to 6 and m is an integer from 0 to 34;
D is a halide ion;
L is a linkage derived from a dihalide, x and y are integers ranging from 1-100 and Q is $(BL)_y$ where the bonds between L and A or B are carbon-nitrogen bonds formed by quaternization of the tertiary amine functions of A and B by the organic dihalides from which L is derived and W is 0 or 1; which are obtained by first forming a block of units by reacting a monomer of the formula II

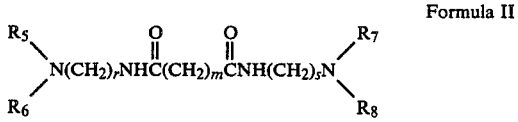
Formula II wherein
each of $R_5$, $R_6$, $R_7$ and $R_8$ may be the same or different and is selected from the group consisting of $C_{1-3}$ alkyl, $C_{1-3}$ hydroxy alkyl and hyroxy polyalkylene,
m is an integer from 0 to 34 and
r and s are the same or different and are integers from 1 to 6,
with a molar excess of a dihalide of the formula

Hal—L—Hal wherein Hal represents a halogen atom and L is selected from —$CH_2CH_2$—O—$CH_2CH_2$—, —$CH_2CH_2$—O—$CH_2CH_2$—O—$CH_2CH_2$—, —$(CH_2)_t$— and —$CH_2CHOHCH_2$— where t is an integer from 2 to 6 and thereafter reacting the product so formed with a compound of the formula III

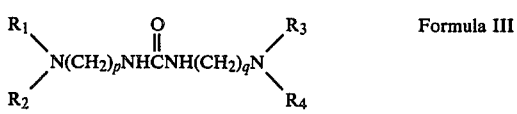
Formula III wherein $R_1$, $R_2$, $R_3$ and $R_4$ are each individually selected from the group consisting of $C_{1-3}$ alkyl, $C_{1-3}$ hydroxyalkyl and hydroxy polyalkylene and p, and q are each individually integers of from 1 to 6 and, if necessary, in order to ensure a total molar ratio of compounds of Formulae II and III to those of the formula Hal—L—Hal of 1:1, reacting the product with further compound of the formula Hal—L—Hal.

Most suitably L is the residue of a dihalide such as $ClCH_2CH_2OCH_2CH_2Cl$, $ClCH_2CH_2$—O—$CH_2CH_2$—O—$CH_2CH_2Cl$, $ClCH_2CH_2Cl$, $BrCH_2CH_2Br$, $Cl(CH_2)_6Cl$, $ClCH_2CH_2CH_2Cl$ and $ClCH_2CH(OH)CH_2Cl$.

Desirably the overall ratio of B residues to A residues is from 0.66 to 19:1 preferably 3 to 19:1. The number of L residues equals to total number of A and B residues.

$R_1$, $R_2$, $R_3$, $R_4$, $R_5$, $R_6$, $R_7$ and $R_8$ are preferably each individually alkyl and are typically methyl or ethyl,
p, q, r and s are each typically 2, 3 or 4;
m is preferably 3–10, typically 4–7.

The products of the present invention preferably have a molecular weight in excess of 20,000 typically in the range 20,000 to 50,000 as determined by end group analysis titration, assuming that all end groups are tertiary amine.

Sufficient dihalide is used for the overall process so that the molar amount of Hal—L—Hal is equal to the total molar amounts of Formula II plus Formula III.

DETAILED DESCRIPTION OF THE INVENTION

Monomers of formula III may be obtained as described in U.S. Pat. No. 4,157,388 (Christiansen, issued Jan. 5, 1979), the contents whereof are incorporated herein by reference.

Monomers of formula II are obtained by condensation of amines of the formula

Formula IV and

Formula V with a dicarboxylic acid of the formula $HOOC(CH_2)_mCOOH$ or a reactive derivative thereof as described in commonly assigned copending Application Ser. No. 758,483 filed on July 24, 1985, which is incorporated herein by reference.

The production of the compounds of the present invention will now be described with reference to copolymers containing the preferred repeating units namely those wherein recurring group A is derived from a monomer of the formula

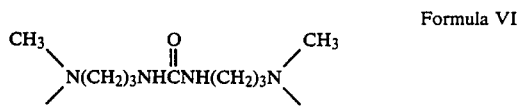
Formula VI recurring group B is derived from a monomer of the formula

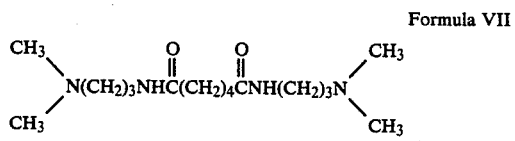

Formula VII and L is —CH$_2$CH$_2$—O—CH$_2$CH$_2$—.

It will, however, be appreciated that the techniques described herein are equally applicable to the production of copolymers wherein A, B and L have different values.

Typically a monomer of formula VII is heated in an aqueous medium to from 60°–100° C., preferably about 90°–100° C. and a molar excess of 2,2'-bis chloroethyl ether added slowly, typically over a period of one to three hours. The excess of the dichloro ether should not exceed 25% but will depend upon the ratio of A and B units in the final product, so that if the ratio of B to A is 0.66:1 a 25% molar excess of the dichloro ether may be used whereas if the final ratio of B to A units is 19:1 a molar excess of the dichloro ether of only about 10% will be satisfactory. Once addition of the dichloroether has been completed, heating of the reaction mixture is continued for several hours (typically 6 to 10 hours). Monomer of formula VI is then added followed by additional 2,2'bis(chloroethyl)ether in an amount to result in a 1:1 molar ratio of said ether to the total number of moles of monomers of formulae VI and VII. The reaction mixture is then maintained at elevated temperature, typically in the range of 90° to 100° C. until the ratio of ionic chloride to total chloride exceeds 0.99:1. Such a determination of the amount of ionic chloride can be made, for example by potentiometric titration.

Generally, reactions are conducted in such a way that virtually all of the organic dihalide is consumed or removed from the product. In this way, essentially all end groups of the polymer chains are tertiary amino groups. A variant of this procedure may be used when the ratio of monomer of formula VII used to monomer of formula VI exceeds 9:1. In that case all of the 2,2'bis(chloroethyl)ether may be added to the compound of formula VII before addition of compound of formula VI.

Typical products according to the invention have a molar ratio of B to A units in the range 1:1 to 9:1.

The block copolymers of the present invention are most usefully prepared in an aqueous medium having a solids content of 40 to 75 percent, preferably 60 to 65%. Such concentration may be obtained by addition of water to the reaction product or distilling water from the reaction product as desired.

The pH of the products is desirably in the range 6 to 9 for a 10% solution, more preferably in the range 7 to 9, commonly about 8.5

The block copolymers of the present invention may be used in a wide variety of applications. They can be used in formulations in which anionic materials are present, although special formulation techniques may be required in such cases. For example the valuable antistatic properties of the products are of use not only in laundry detergents but also in shampoo formulations and textile treatments.

For example we have found that repeated washing using a conventional liquid built anionic laundry detergent or non-ionic laundry detergents to which the block copolymers of the present invention have been added results in a substantial decrease in static after each washing.

The block copolymers of the present invention may be employed in detergent formulations comprising a variety of conventional detergent materials including anionic materials such as alkyl benzene sulfonates, olefin sulfonates, fatty alcohol sulfates, alkylene oxide sulfates and fatty alcohol alkylene oxide sulfates and non-ionic materials such as alkylene oxide polymers, alkoxylated phenols and alkylolamides as well as builders such as sodium sulfate, sodium silicate and, where permitted, sodium phosphates such as sodium tripolyphosphate.

The antistatic properties of the block copolymers of the present invention are also of use in shampoo formulations, for example with mild anionic surfactants such as sodium salts of acids of alkoxylated fatty alcohols, non-ionic detergents such as polyoxyalkylene glycols and fatty alcohol alkylene oxide adducts and cationic surfactants such as a quaternized fatty amines. A further use is in textile finishing in which a fabric is passed through a bath containing a wetting agent and a copolymer of the present invention to improve its antistatic properties.

Flocculating compositions comprising the block copolymers of the present invention commonly also include salts such as sodium sulfate and sodium chloride. Such compositions find use inter alia in flocculation of materials such as clays and for example in water purification treatments and in the treatment of aqueous effluents.

The production and use of the copolymers of the present invention are illustrated by the following examples and experiments.

EXAMPLES 1–5

The following general technique was employed to prepare block copolymers.

In all cases condensate A was

condensate B was

wherein n was 4 when the condensate was prepared from adipic acid and 7 when the condensate was prepared from azaleic acid. The number of moles (X) of condensate B used varied from 0.4 to 0.95 and the number of moles (Y) of condensate A varied from 0.6 to 0.05 so that the total number of moles of A and B used was 1.0. Water was used in an amount to give about 65% solids.

The water and Condensate B (X mole) were charged to a reaction flask equipped with mechanical stirrer, reflux condenser, thermometer and addition funnel. This mixture was heated to 90° C., and 2,2'-bis(chloroethyl)ether (X+0.1 mole) was added over a period of 1–3 hours while maintaining a reaction temperature of 90°–100° C. When addition was complete, the temperature was maintained at 90°–100° C. for 6–10 hours then Condensate A (Y mole) was added. Additional 2,2'-bis(- chloroethyl)ether (Y−0.1 mole) was then added over a period of 1–3 hours while maintaining 90°–100° C. reaction temperature. [It should be noted that when X=0.9, this second addition of the ether was not made and the first addition was a maximum of 1.0 mole.] When this addition was complete, reaction temperature was maintained at 90°–100° C. until the ratio of ionic chloride to total chloride as measured by potentiometric titration was greater than 0.59. Heating was continued until a ratio of >0.99 is obtained. When this occured, the pH was adjusted to the desired range (generally between 6 and 9 for a 10% solution) and water distilled off (or added) to achieve the desired concentration of active product (generally 60 to 65% solids).

| Example | Condensate B Moles | Diacid used | Condensate A Moles | Product % Solids | pH |
|---|---|---|---|---|---|
| 1 | 0.9 | Azelaic | 0.1 | 64.1 | 8.5 |
| 2 | 0.9 | Adipic | 0.1 | 63.9 | 8.7 |
| 3 | 0.75 | Adipic | 0.25 | 64.4 | 7.4 |
| 4 | 0.5 | Adipic | 0.5 | 65.2 | 8.5 |
| 5 | 0.3 | Adipic | 0.7 | 62.5 | 8.5 |

COMPARATIVE EXPERIMENTS

The following are examples of block copolymers made by the procedure described, except that Condensate A was reacted first, followed by reaction with B:

| Comparative Experiment | Condensate B Moles | Diacid used | Condensate A Moles | Product % Solids | pH |
|---|---|---|---|---|---|
| 1 | 0.4 | Azelaic | 0.6 | 69.2 | 8.7 |
| 2 | 0.2 | Azelaic | 0.8 | 61.5 | 8.7 |

In addition, the following are examples of random copolymers. These were made by combining Condensate A and Condensate B in the mole ratios indicated and reacting them with 1.0 mole of 2,2'-bis(chloroethyl)ether in water at 90°–100° C. until the ratio of ionic chloride to total chloride ws >0.99.

| Comparative Experiment | Condensate B Moles | Diacid used | Condensate A Moles | Product % Solids | pH |
|---|---|---|---|---|---|
| 3 | 0.9 | Azelaic | 0.1 | 66.6 | 7.9 |
| 4 | 0.4 | Azelaic | 0.6 | 62.4 | 9.0 |
| 5 | 0.2 | Azelaic | 0.8 | 61.9 | 9.2 |
| 6 | 0.75 | Adipic | 0.25 | 64.3 | 8.1 |

The use of the compounds of the present invention and the improved properties thereof as compared to the compounds of the comparative experiments are illustrated by the following Examples.

EXAMPLE 6

Antistatic Test

The following test was run using wool as a model for hair. Test results demonstrate substantivity and antistatic properties of the various products.

Strips (about 1½×4 inches) of clean wool soil cloth were immersed in 5.0% solids solutions of the various products for a period of 5 minutes then separately oven dried (50° C.) for 30 minutes. After equilibrating to the ambient atmosphere for 30 minutes, the antistatic test was run (result I).

The same cloth strips were then rinsed twice with water, oven dried and allowed to equilibrate as before and again tested for static (result II). Finally, the cloth strips were immersed in a 2% solids solution of baby shampoo for 5 minutes, rinsed twice with water, oven dried and allowed to equilibrate as before and again tested for static (result III).

The test for static comprises vigorously stroking the cloth strip 40 times in one direction with a glass rod while the strip is held at one end and resting on a paper towel on a table. The strip is then held about ½ inch above a watch glass containing either finely pulverized cigarette or cigar ashes or crumbled polystyrene packing "saddles". Negative results (no attraction of ashes or polystyrene) means good antistatic properties whereas positive results (attraction) means poor antistatic properties. Results for the various materials tested are tabulated below.

| Product | Result I | Result II | Result III |
|---|---|---|---|
| Example 1 | − | − | − |
| Example 2 | − | − | − |
| Example 3 | − | − | − |
| Example 4 | − | − | − |
| Example 5 | − | + | + |
| Comparative Experiment 1 | − | + | + |
| Comparative Experiment 2 | − | + | + |
| Comparative Experiment 3 | − | − | + |
| Comparative Experiment 4 | − | + | + |
| Comparative Experiment 5 | − | + | + |
| Comparative Experiment 6 | − | + | + |
| MIRAPOL ® A-15[a] | − | + | + |
| MIRAPOL ® AD-1[b] | − | + | + |
| MIRAPOL ® AZ-1[c] | − | + | + |
| Water (control) | + | + | + |

[a]Product described in U.S. Pat. No. 4,157,388
[b]Product from adipic acid described in U.S. Application 758,483
[c]Product from azelaic acid described in U.S. Application 758,483

EXAMPLE 7

Clay Compaction test

Test solutions were made up as follows:

| | % by weight |
|---|---|
| Polymer (as is solution) | 0.2 |
| NaH$_2$PO$_4$ | 0.12 |
| Distilled water | 99.68 |
| pH is 5.0–5.9 | |

To 2.0 g of clay (Accu-Gel F, American Colloid Co.) in a calibrated (to 1 cc intervals) 50 cc centrifuge tube was added 40 cc of test solution. After allowing to stand for 15 minutes the mixture was centrifuged for 5 minutes. The supernatant liquid was decanted and 41 cc of distilled water added. This was allowed to stand for 5 minutes, centrifuged for 5 minutes, then the volume of clay solids measured. The average of duplicate measurements for the various polymers is tabulated below:

| Polymer | Clay Volume (cc) | Polymer | Clay Volume (cc) |
|---|---|---|---|
| Example 1 | 8 | Comp. Exp. 4 | 9 |
| Example 2 | 3.5 | Comp. Exp. 5 | 10 |
| Example 3 | 3.5 | Comp. Exp. 6 | 9 |
| Example 4 | 4 | MIRAPOL ® A-15 | 5 |
| Example 5 | 4.5 | MIRAPOL ® AD-1 | 8 |
| Comparative Experiment 1 | 8 | MIRAPOL ® AZ-1 | 8 |
| Comparative Experiment 2 | 8 | Water (control) | 9 |

| Polymer | Clay Volume (cc) | Polymer | Clay Volume (cc) |
|---|---|---|---|
| Comparative Experiment 3 | 9 | | 5 |

EXAMPLE 8

Test solutions were made by adding 5 g of product from Example 2 to 100 g of Wisk detergent and 5 g of product from Example 2 to 100 g Dynamo detergent. Similar solutions were made using the product from Example 3. Wisk is a built anionic detergent and is a hazy liquid. Dynamo is a nonionic-based detergent and is clear. Addition of the copolymers produced no visible effect on the appearance of either detergent. Storage of samples for 4 weeks at ambient temperature or at 50° C. also showed no change in appearance.

Strips (about 1½×4 inches) of clean wool soil cloth and clean cotton soil cloth were independently washed in the four detergent samples (5 g detergent in 200 g water). The eight cloth strips were each rinsed twice with fresh water then separately oven dried at 50° C. After allowing them to equilibrate to room conditions (~½ hour) they were tested for static using the procedure described in Example 7.

This procedure was repeated two more times, each time using the same detergent system with the same cloth strip as before. In all cases, the following order of anti-static performance was found:

3rd wash > 2nd wash > 1st wash

Repeated washing with detergent alone resulted in no observable antistatic effect.

These results demonstrate the potential for use of these block copolymers as detergent-compatible softener-antistats in anionic as well as nonionic based detergents.

The invention claimed is:

1. Block copolymer of the formula:

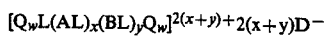

wherein
A is

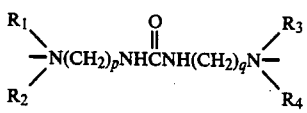

and B is

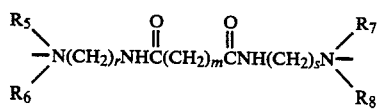

wherein:
$R_1$, $R_2$, $R_3$, $R_4$, $R_5$, $R_6$, $R_7$, and $R_8$ are the same or different and are selected from the group consisting of $C_1$-$C_3$ alkyl, $C_1$-$C_3$ hydroxyalkyl, or hydroxy polyoxyalkylene;
D is a halide ion;
L is a linkage derived from a dihalide after removal of the halogen atoms, x and y are integers ranging from 1–100 and Q is $(BL)_y$ where the bonds between L and A or B are carbon-nitrogen bonds formed by quaternization of the tertiary amine functions of A or B by the organic dihalides from which L is derived and W is 0 or 1 which are obtained by first forming a block of units by reacting a monomer of the formula II

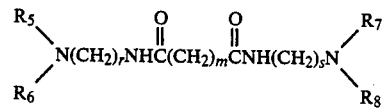

wherein
each of $R_5$, $R_6$, $R_7$ and $R_8$ are the same or different and is selected from the group consisting of $C_{1-3}$ alkyl, $C_{1-3}$ hydroxy alkyl hydroxy polyoxyalkylene,
m is an integer from 0 to 34 and
r and s are the same or different and are integers from 1 to 6,
with a molar excess of a dihalide of the formula

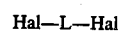

wherein Hal represents a halogen atom and L is selected from —$CH_2CH_2$—O—$CH_2CH_2$—, —$CH_2CH_2$—O—$CH_2CH_2$—O—$CH_2CH_2$—, —$(CH_2)_t$— or —$CH_2CHOHCH_2$— where t is an integer from 2 to 6 and thereafter reacting the product so formed with a compound of the formula III

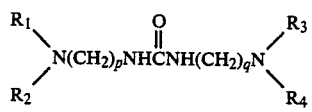

wherein $R_1$, $R_2$, $R_3$ and $R_4$ are each individually selected from the group consisting of $C_{1-3}$ alkyl, $C_{1-3}$ hydroxyalkyl and polyoxyalkylene and p, and q are each individually integers of from 1 to 6 and, if the amount of compound of the formula Hal—L—Hal used in the first reaction was not sufficient to ensure a total molar ratio of compounds of Formulae II and III to those of the formula Hal—L—Hal of 1:1, reacting the product with further compound of the formula Hal—L—Hal.

2. Block copolymer according to claim 1, wherein the ratio of B units to A units is in the range 0.66 to 19:1.

3. Block copolymer according to claim 2, wherein the ratio of B units to A units is in the range 3 to 9:1.

4. Block copolymer according to claim 1, wherein $R_1$, $R_2$, $R_3$, $R_4$, $R_5$, $R_6$, $R_7$, and $R_8$, are each individually alkyl.

5. Block copolymer according to claim 4, wherein $R_1$, $R_2$, $R_3$, $R_4$, $R_5$, $R_6$, $R_7$, and $R_8$, are each individually methyl or ethyl.

6. Block copolymer according to claim 1, wherein each of p, q, r, and s is from 2 to 4.

7. Block copolymer according to claim 1, wherein m is 4 to 7.

8. Block copolymer according to claim 1, wherein L is selected from the group consisting of —$CH_2CH_2$—O$CH_2CH_2$—, —$CH_2CH_2$—O—$CH_2CH_2$—O—$CH_2CH_2$—, —$(CH_2)_t$— and —$CH_2CH(OH)CH_2$— where t is an integer from 2 to 6.

9. Block copolymer according to claim 1, wherein A is

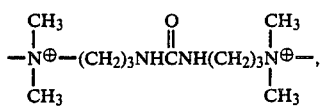

B is

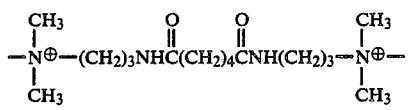

and L is

10. A process for preparing block copolymers which comprises first forming a block of units by reacting a monomer of the formula II

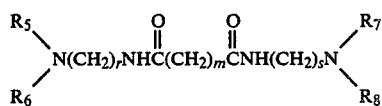

wherein
each of $R_5$, $R_6$, $R_7$ and $R_8$ may be the same or different and is selected from the group consisting of $C_{1-3}$ alkyl, $C_{1-3}$ hydroxy alkyl and polyoxyalkylene, m is an integer from 0 to 34 and
r and s are the same or different and are integers from 1 to 6,
with a molar excess of a dihalide of the formula Hal—L—Hal wherein Hal represents a halogen atom and L is selected from —CH$_2$CH$_2$—O—CH$_2$CH$_2$—, —CH$_2$CH$_2$—O—CH$_2$CH$_2$—O—CH$_2$CH$_2$—, —(CH$_2$)$_t$— and —CH$_2$CHOHCH$_2$— where t is an integer from 2 to 6 and thereafter reacting the product so formed with a compound of the formula III

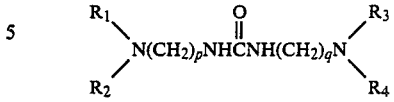

wherein $R_1$, $R_2$, $R_3$ and $R_4$ are each individually selected from the group consisting of $C_{1-3}$ alkyl, $C_{1-3}$ hydroxyalkyl and polyoxyalkylene and p, and q are each individually integers of from 1 to 6 and, if the amount of compound of the formula Hal—L—Hal used in the first reaction was not sufficient, in order to ensure a total molar ratio of compounds of Formulae II and III to those of the formula Hal—L—Hal of 1:1 reacting the product with further compound of the formula Hal—L—Hal.

11. A process according to claim 10, wherein the molar ratio of compound of Formula II to compound of Formula III is from 0.66 to 19:1.

12. A process according to claim 10, wherein the excess of compound of formula Hal—L—Hal over compound of formula II used in the first stage of the reaction is in the range 10 to 25 molar percent.

13. A process according to claim 10, wherein the molar ratio of compound of formula II to formula III used is greater than 9:1 and in the initial reaction of compound of formula II with compound of the formula Hal—L—Hal, the amount of the latter compound employed is the amount required to result in a 1:1 molar ratio of compound of formula Hal—L—Hal to the total of compounds of formulae II and III.

14. A process according to claim 10, which is conducted in an aqueous medium at a temperature in the range 90°–100° C.

15. A process according to claim 10, wherein after the reaction is completed the pH of the product is adjusted to bring it into the range 6 to 9 for a 10% aqueous solution.

16. A detergent composition which contains a block copolymer as claimed in claim 1.

* * * * *